(12) United States Patent
Begg (10) Patent No.: US 11,622,787 B2
(45) Date of Patent: Apr. 11, 2023

(54) FLUID-DRIVEN TISSUE RESECTING INSTRUMENTS, SYSTEMS, AND METHODS

(71) Applicant: Covidien LP, Mansfield, MA (US)

(72) Inventor: Nikolai D. Begg, Wellesley, MA (US)

(73) Assignee: Covidien LP, Mansfield, MA (US)

( * ) Notice: Subject to any disclaimer, the term of this patent is extended or adjusted under 35 U.S.C. 154(b) by 389 days.

(21) Appl. No.: 17/021,137

(22) Filed: Sep. 15, 2020

(65) Prior Publication Data

US 2020/0405339 A1    Dec. 31, 2020

Related U.S. Application Data

(62) Division of application No. 15/900,073, filed on Feb. 20, 2018, now Pat. No. 10,772,654.

(Continued)

(51) Int. Cl.
*A61B 17/32* (2006.01)
*A61B 17/42* (2006.01)
(Continued)

(52) U.S. Cl.
CPC .... *A61B 17/32002* (2013.01); *A61B 17/3203* (2013.01); *A61B 17/42* (2013.01);
(Continued)

(58) Field of Classification Search
CPC .......... A61B 17/32002; A61B 17/3203; A61B 17/42; A61B 2017/00477;
(Continued)

(56) References Cited

U.S. PATENT DOCUMENTS

| | | | |
|---|---|---|---|
| 1,585,934 A | 5/1926 | Muir | |
| 1,666,332 A | 4/1928 | Hirsch | |

(Continued)

FOREIGN PATENT DOCUMENTS

| | | | |
|---|---|---|---|
| DE | 3339322 A1 | 5/1984 | |
| DE | 3206381 C2 | 7/1986 | |

(Continued)

OTHER PUBLICATIONS

Exended European Search Report issued in corresponding European application No. 18159257.7 dated Jun. 1, 2018, 7 pages.

(Continued)

*Primary Examiner* — Timothy J Neal
*Assistant Examiner* — Andrew P. Restaino
(74) *Attorney, Agent, or Firm* — Carter, DeLuca & Farrell LLP (57) ABSTRACT

A tissue resecting instrument includes a housing, a shaft rotatable relative to the housing and defining a proximal end portion disposed within the housing and a distal end portion distally-spaced from the housing, a cutting member operably associated with the distal end portion of the shaft, a turbine disposed within the housing and operably associated with the proximal end portion of the shaft, and a fluid outflow tube operably associated with the housing. The fluid outflow tube is adapted to connect to a suction source to enable the suctioning of fluid and resected tissue proximally through a lumen of the shaft, an interior of the housing, and into the fluid outflow tube. The turbine is configured such that proximal fluid flow across the plurality of fins of the turbine urges the turbine to rotate, thereby rotating the shaft relative to the housing to enable tissue resection with the cutting member.

17 Claims, 5 Drawing Sheets

Related U.S. Application Data (60) Provisional application No. 62/465,907, filed on Mar. 2, 2017.

(51) Int. Cl.
  *A61M 3/02* (2006.01)
  *A61B 17/3203* (2006.01)
  *A61B 17/00* (2006.01)

(52) U.S. Cl.
  CPC . *A61M 3/0283* (2013.01); *A61B 2017/00477* (2013.01); *A61B 2017/00553* (2013.01); *A61B 2017/320032* (2013.01); *A61B 2017/4216* (2013.01); *A61B 2217/005* (2013.01); *A61B 2217/007* (2013.01); *A61M 2210/1433* (2013.01)

(58) Field of Classification Search
  CPC ......... A61B 2017/00553; A61B 2017/320032; A61B 2017/4216; A61B 2217/005; A61B 2217/007; A61M 3/0283; A61M 2210/1433; A61M 1/85
  See application file for complete search history.

(56) References Cited

U.S. PATENT DOCUMENTS

| | | |
|---|---|---|
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,906,954 A | 9/1975 | Baehr |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,281,457 A | 8/1981 | Walton, II |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,895,560 A | 1/1990 | Papantonakos |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |

(56) References Cited

U.S. PATENT DOCUMENTS

| | | |
|---|---|---|
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,491,660 B2 | 12/2002 | Guo et al. |
| 6,494,892 B1 | 12/2002 | Ireland et al. |
| 6,511,493 B1 | 1/2003 | Moutafis et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 6,875,221 B2 | 4/2005 | Cull |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,061,359 B2 | 11/2011 | Emanuel |
| 8,062,214 B2 | 11/2011 | Shener et al. |
| 8,419,626 B2 | 4/2013 | Shener-Irmakoglu et al. |
| 8,663,264 B2 | 3/2014 | Cesarini et al. |
| 8,678,999 B2 | 3/2014 | Isaacson |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,033,864 B2 | 5/2015 | Furlong et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,125,550 B2 | 9/2015 | Shener-Irmakoglu et al. |
| 9,155,454 B2 | 10/2015 | Sahney et al. |
| 9,636,130 B2 | 5/2017 | Cesarini et al. |
| 2001/0039963 A1 | 11/2001 | Spear et al. |
| 2001/0047183 A1 | 11/2001 | Privitera et al. |
| 2002/0058859 A1 | 5/2002 | Brommersma |
| 2002/0165427 A1 | 11/2002 | Yachia et al. |
| 2003/0050603 A1 | 3/2003 | Todd |
| 2003/0050638 A1 | 3/2003 | Yachia et al. |
| 2003/0078609 A1 | 4/2003 | Finlay et al. |
| 2003/0114875 A1 | 6/2003 | Sjostrom |
| 2004/0204671 A1 | 10/2004 | Stubbs et al. |
| 2005/0043690 A1 | 2/2005 | Todd |
| 2005/0085692 A1 | 4/2005 | Kiehn et al. |
| 2006/0036132 A1 | 2/2006 | Renner et al. |
| 2006/0047185 A1 | 3/2006 | Shener et al. |
| 2006/0241586 A1 | 10/2006 | Wilk |
| 2008/0001562 A1 | 1/2008 | Hobbet et al. |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0121141 A1 | 5/2010 | Rontal |
| 2010/0152647 A1 | 6/2010 | Shener et al. |
| 2011/0166419 A1 | 7/2011 | Reif et al. |
| 2012/0078038 A1 | 3/2012 | Sahney et al. |
| 2013/0131452 A1 | 5/2013 | Kuroda et al. |
| 2013/0218186 A1 | 8/2013 | Dubois et al. |
| 2014/0031834 A1 | 1/2014 | Germain et al. |
| 2016/0312787 A1 | 10/2016 | Sato |

(56) References Cited

U.S. PATENT DOCUMENTS

| | | |
|---|---|---|
| 2017/0027637 A1 | 2/2017 | Germain et al. |
| 2017/0108238 A1 | 4/2017 | McMahon |
| 2018/0368872 A1 | 12/2018 | Fukui |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 19751632 C1 | 9/1999 |
| DE | 102006022827 A1 | 12/2006 |
| EP | 0147192 A2 | 7/1985 |
| EP | 0310285 A2 | 4/1989 |
| EP | 0327410 A1 | 8/1989 |
| EP | 0338965 A1 | 10/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1681022 A1 | 7/2006 |
| GB | 2093353 A | 9/1982 |
| GB | 2311468 A | 10/1997 |
| JP | 2002529185 A | 9/2002 |
| JP | 2002538889 A | 11/2002 |
| JP | 2003245247 A | 9/2003 |
| NL | 1006944 C2 | 3/1999 |
| WO | 8101648 A1 | 6/1981 |
| WO | 9211816 A2 | 7/1992 |
| WO | 9307821 A1 | 4/1993 |
| WO | 9315664 A1 | 8/1993 |
| WO | 9426181 A1 | 11/1994 |
| WO | 9505777 A1 | 3/1995 |
| WO | 9510981 A1 | 4/1995 |
| WO | 9510982 A1 | 4/1995 |
| WO | 9522935 A1 | 8/1995 |
| WO | 9530377 A1 | 11/1995 |
| WO | 9611638 A1 | 4/1996 |
| WO | 9626676 A1 | 9/1996 |
| WO | 9709922 A1 | 3/1997 |
| WO | 9717027 A1 | 5/1997 |
| WO | 9719642 A1 | 6/1997 |
| WO | 9724071 A1 | 7/1997 |
| WO | 9734534 A1 | 9/1997 |
| WO | 9735522 A1 | 10/1997 |
| WO | 9809569 A1 | 3/1998 |
| WO | 9810707 A1 | 3/1998 |
| WO | 9846147 A1 | 10/1998 |
| WO | 9903407 A1 | 1/1999 |
| WO | 9903409 A1 | 1/1999 |
| WO | 9907295 A1 | 2/1999 |
| WO | 9911184 A1 | 3/1999 |
| WO | 9939648 A1 | 8/1999 |
| WO | 9944506 A1 | 9/1999 |
| WO | 9960935 A1 | 12/1999 |
| WO | 0012010 A1 | 3/2000 |
| WO | 0028890 A1 | 5/2000 |
| WO | 0033743 A1 | 6/2000 |
| WO | 0044295 A1 | 8/2000 |
| WO | 0047116 A1 | 8/2000 |
| WO | 0057797 A1 | 10/2000 |
| WO | 0135831 A1 | 5/2001 |
| WO | 0158368 A1 | 8/2001 |
| WO | 0195810 A2 | 12/2001 |
| WO | 02069808 A2 | 9/2002 |
| WO | 03022164 A1 | 3/2003 |
| WO | 03077767 A1 | 9/2003 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 2007044833 A2 | 4/2007 |
| WO | 2012044705 A1 | 4/2012 |
| WO | 2017007851 A1 | 1/2017 |

OTHER PUBLICATIONS

European Examination Report dated Mar. 24, 2020 issued in corresponding EP Appln. No. 18 159 257.7, 5 pages.

FLUID-DRIVEN TISSUE RESECTING INSTRUMENTS, SYSTEMS, AND METHODS

CROSS REFERENCE TO RELATED APPLICATION

The present application is a divisional of U.S. patent application Ser. No. 15/900,073, filed Feb. 20, 2018, which claims the benefit of and priority to U.S. Provisional Application Ser. No. 62/465,907, filed on Mar. 2, 2017 the entire contents of which are incorporated herein by reference.

BACKGROUND

1. Technical Field

The present disclosure relates generally to the field of tissue resection. In particular, the present disclosure relates to fluid-driven tissue resecting instruments, systems, and methods.

2. Background of Related Art

Tissue resection may be performed endoscopically within an organ, such as a uterus, by inserting an endoscope into the uterus and passing a tissue resection device through the endoscope and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space.

If the outflow of fluid from the uterus is greater than the inflow of fluid, the uterus may collapse, making visualization and tissue resection difficult. On the other hand, if the inflow of fluid is greater than the outflow of fluid, excess fluid can enter the patient's vascular system and result in serious complications or death. Thus, the inflow and outflow of fluid to/from the uterus is controlled to maintain proper distension of the uterus during the tissue resection procedure. This may be accomplished utilizing using a fluid pump (to pump the inflow flow) and/or fluid suction source (to suction the outflow fluid) in connection with one or more valves, switches, and/or other regulating devices.

In addition to the fluid pumps, fluid suction sources, valves, and/or other regulating devices utilized to maintain appropriate fluid inflow and fluid outflow, tissue resecting instruments and systems typically employ a separate motor to drive the cutter of the tissue resecting instrument to resect tissue.

SUMMARY

As used herein, the term "distal" refers to the portion that is described which is further from a user, while the term "proximal" refers to the portion that is described which is closer to a user. Further, to the extent consistent, any or all of the aspects described herein may be used in conjunction with any or all of the other aspects described herein.

Provided in accordance with aspects of the present disclosure is a tissue resecting instrument including a housing defining an interior, a shaft, a cutting member, a turbine, and a fluid outflow tube. The shaft is rotatable relative to the housing and extends distally from the housing. The shaft defines a proximal end portion disposed within the interior of the housing, a distal end portion distally-spaced from the housing, and a lumen extending therethrough that is disposed in fluid communication with the interior of the housing. The cutting member is operably associated with the distal end portion of the shaft to enable tissue resection upon rotation of the shaft. The turbine is disposed within the interior of the housing and operably associated with the proximal end portion of the shaft such that rotation of the turbine rotates the shaft relative to the housing. The turbine includes a plurality of fins. The fluid outflow tube is operably associated with the housing and adapted to connect to a suction source to enable the suctioning of fluid and resected tissue proximally through the lumen of the shaft, the interior of the housing, and into the fluid outflow tube. The turbine is configured such that proximal fluid flow across the plurality of fins of the turbine urges the turbine to rotate, thereby rotating the shaft relative to the housing to enable tissue resection with the cutting member.

In an aspect of the present disclosure, the cutting member is fixedly engaged to the shaft such that rotation of the shaft rotates the cutting member to resect tissue therewith.

In another aspect of the present disclosure, a fixed outer tube is disposed about the shaft. The fixed outer tube is fixed relative to and extends distally from the housing. The shaft is rotatable relative to the fixed outer tube to enable tissue resection with the cutting member.

In yet another aspect of the present disclosure, the turbine includes a tubular body disposed about the proximal end portion of the shaft. The fins of the turbine are arranged annularly about the tubular body and extend radially outwardly therefrom.

In still another aspect of the present disclosure, the turbine includes a conical body disposed about the proximal end portion of the shaft and oriented such that a nose end of the conical body is disposed more-distally and a base end of the conical body is disposed more-proximally. The fins of the turbine are arranged about the conical body and extend radially outwardly therefrom.

In still yet another aspect of the present disclosure, the proximal end portion of the shaft defines a plurality of openings therethrough that enable fluid communication between the lumen of the shaft and the interior of the housing.

In another aspect of the present disclosure, the cutting member defines an opening therethrough in communication with the lumen of the shaft. The cutting member further includes a tissue cutting edge surrounding the opening.

In yet another aspect of the present disclosure, the turbine includes a thrust coupling that couples the turbine to the proximal end portion of the shaft.

A tissue resecting system provided in accordance with aspects of the present disclosure includes a tissue resecting instrument, an outer sheath, a fluid pump, and a fluid suction source. The tissue resecting instrument includes a housing, a shaft extending distally from the housing, a cutting member operably associated with a distal end portion of the shaft, and a turbine disposed within the housing and operably associated with the cutting member such that rotation of the turbine rotates the cutting member relative to the housing to enable resection of tissue. The outer sheath is disposed about the shaft so as to define an annular channel between the shaft and the outer sheath. The fluid pump is configured to pump fluid distally through the annular channel and into an internal surgical site. The fluid suction source is configured to suction fluid proximally out of an internal surgical site, through the shaft, and proximally across the turbine within the housing. The proximal fluid flow across the turbine urges the turbine to rotate, thereby rotating the cutting member relative to the housing to enable tissue resection with the cutting member.

In an aspect of the present disclosure, the cutting member is fixedly engaged to the distal end portion of the shaft and the turbine is rotationally fixed to a proximal end portion of the shaft such that rotation of the turbine rotates the shaft to thereby rotate the cutting member. In such aspects, the turbine may include a thrust coupling that couples the turbine to the proximal end portion of the shaft.

In another aspect of the present disclosure, a fixed outer tube is disposed about the shaft. In such aspects, the outer sheath is disposed about the fixed outer tube and the annular channel defined between the shaft and the outer sheath. The fixed outer tube is fixed relative to the housing and the cutting member is rotatable relative to the fixed outer tube.

In still another aspect of the present disclosure, the system further includes a fluid inflow tube coupling the fluid pump with the annular channel and a fluid outflow tube coupling the housing with the fluid suction source.

In yet another aspect of the present disclosure, the turbine includes a tubular body and a plurality of fins arranged annularly about the tubular body and extending radially outwardly therefrom.

In still yet another aspect of the present disclosure, the turbine includes a conical body oriented such that a nose end of the conical body is disposed more-distally and a base end of the conical body is disposed more-proximally. The turbine further includes a plurality of fins arranged about the conical body and extending radially outwardly therefrom.

In another aspect of the present disclosure, the system further includes a fluid supply reservoir operably associated with the fluid pump and a fluid collection reservoir operably associated with the fluid suction source.

A method of resecting tissue provided in accordance with aspects of the present disclosure includes positioning a tissue resecting instrument such that a cutting member of the tissue resecting instrument is disposed within an internal surgical site adjacent tissue to be resected. The tissue resecting instrument includes a turbine operably associated with the cutting member. The turbine is disposed within an outflow path of the tissue resecting instrument. The method further includes pumping fluid distally into the internal surgical site and suctioning fluid proximally out of the internal surgical site through the outflow path of the tissue resecting instrument. Proximal fluid flow across the turbine urges the turbine to rotate, thereby rotating the cutting member to resect tissue adjacent thereto.

In an aspect of the present disclosure, suctioning fluid proximally suctions tissue into the cutting member such that the rotation of the cutting member resects tissue disposed therein, the resected tissue suctioned though the outflow path of the tissue resecting instrument along with fluid.

In another aspect of the present disclosure, pumping fluid distally includes pumping fluid distally through an annular channel defined between a shaft of the tissue resecting instrument and an outer sheath disposed about the shaft.

In another aspect of the present disclosure, pumping fluid distally includes pumping fluid from a fluid supply reservoir distally into the internal surgical site, and/or suctioning fluid proximally includes suctioning fluid proximally out of the internal surgical site through the outflow path of the tissue resecting instrument to a fluid collection reservoir.

BRIEF DESCRIPTION OF THE DRAWINGS

Various aspects and features of the present disclosure are described hereinbelow with reference to the drawings wherein like numerals designate identical or corresponding elements in each of the several views and.

DETAILED DESCRIPTION

Figure 1:
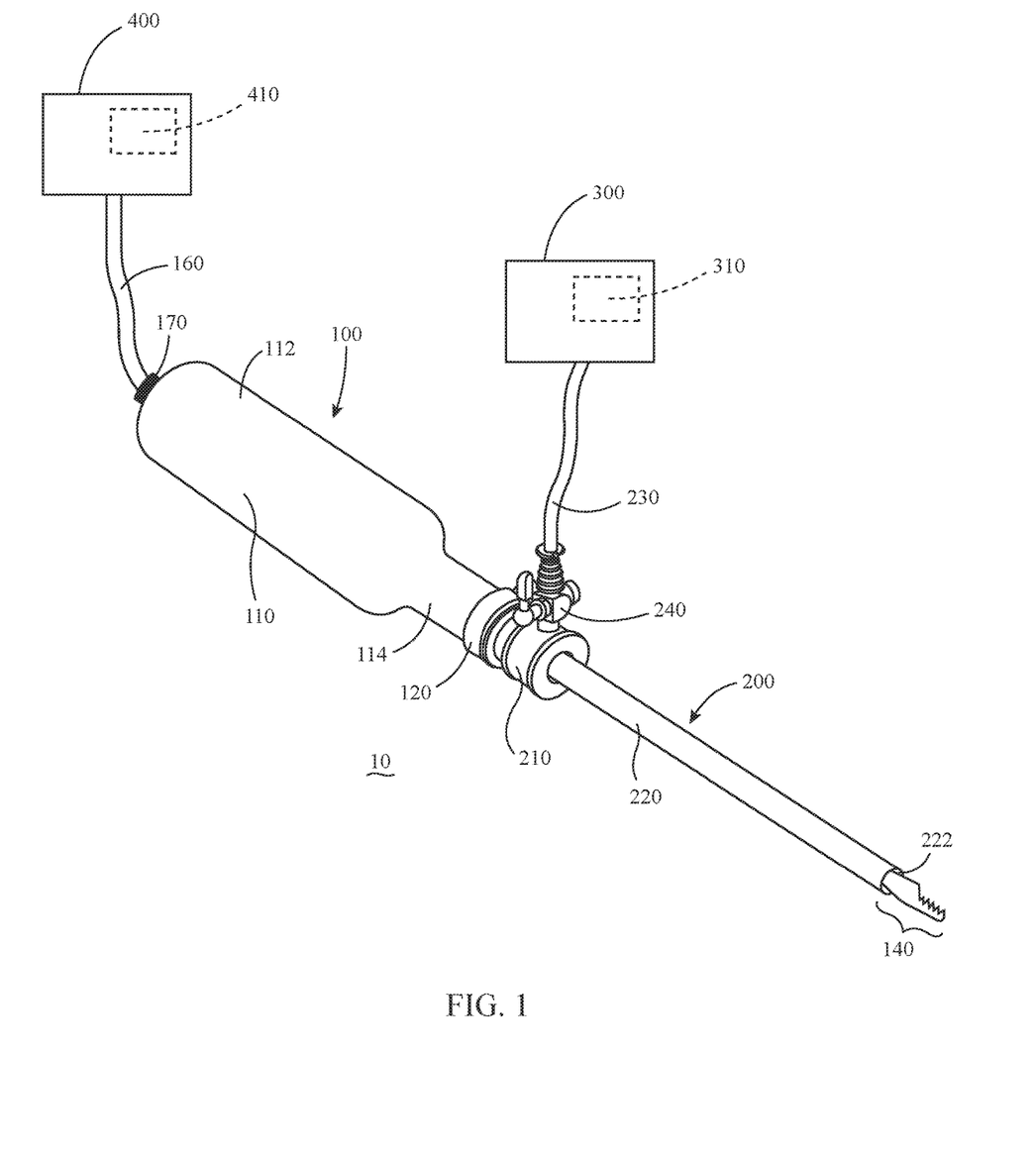
FIG. 1 is a front, perspective view of a tissue resecting system provide in accordance with aspects of the present disclosure.
Figure 2:
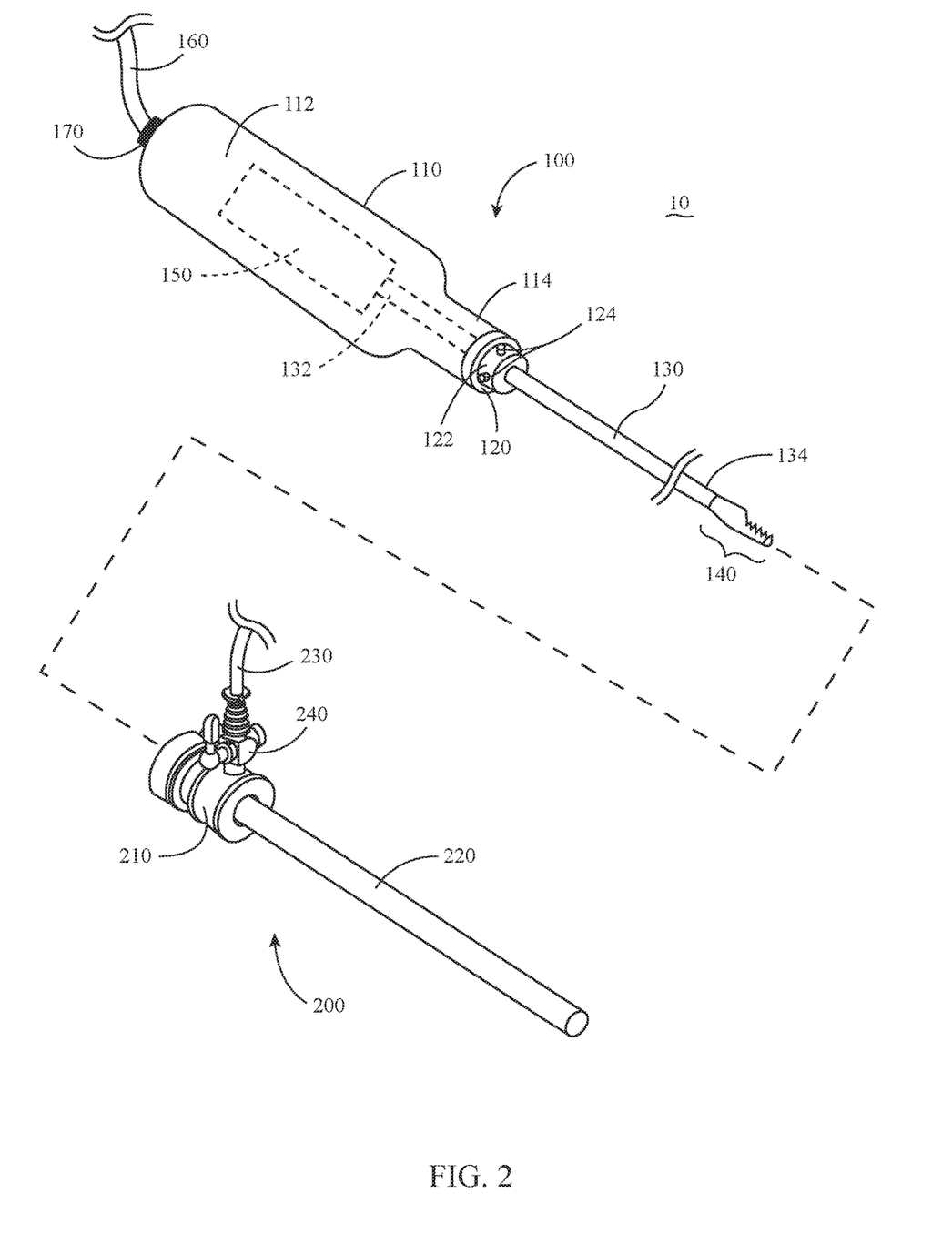
FIG. 2 is an exploded, front, perspective view of the tissue resecting instrument and outer sheath of the tissue resecting system of FIG. 1.

Referring to FIGS. 1 and 2, a tissue resecting system 10 provided in accordance with the present disclosure includes a tissue resecting instrument 100, an outer assembly 200 configured to removably couple to tissue resecting instrument 100 (although, in embodiments, outer assembly 200 may be integral with tissue resecting instrument 100), a fluid pump 300 including a fluid supply reservoir 310 associated therewith, and a suction source 400 including a fluid collecting reservoir 410 associated therewith. Tissue resecting system 10 may be used in conjunction with a suitable endoscope (not shown) or may be used independently thereof. As detailed below, tissue resecting system 10 is configured to facilitate the resection of tissue from within an internal body cavity or organ, e.g., a uterus, while enabling fluid inflow and fluid outflow to maintain proper distension of the uterus during the tissue resection procedure, flush tissue and other debris from within the uterus, and maintain a visible working space.

Tissue resecting instrument 100 of tissue resecting system 10 generally includes a housing 110, an outer sheath connector 120, a shaft 130, a cutting member 140, a drive mechanism 150, and a fluid outflow tube 160. Housing 110 defines a body portion 112 and a distal nose portion 114. Outer sheath connector 120 is disposed on distal nose portion 114 of housing 110 and includes a collar 122 having a plurality of engagement features, e.g., radially-spaced male bayonet connectors 124 extending radially outwardly from collar 122. As detailed below, outer sheath connector 120 is configured to facilitate releasable engagement of outer assembly 200 with tissue resecting instrument 10. Fluid outflow tube 160 communicates with the interior of housing 110 and/or the interior of shaft 130 to enable the withdrawal, e.g., via suction, of fluid, tissue, and other debris from within housing 110 and/or shaft 130. Fluid outflow tube 160 is operably coupled to suction source 400 to enable suction therethrough and for depositing the suctioned fluid, tissue, and other debris into fluid collecting reservoir 410. Fluid outflow tube 160 may further include a valve 170 associated therewith for regulating the outflow of fluid from housing 110 and/or shaft 130.

Shaft 130 of tissue resecting instrument 100 defines a proximal end portion 132 and a distal end portion 134 and is rotatably coupled to housing 110 to enable rotation of shaft 130 relative to housing 110 about a longitudinal axis of shaft 130. Proximal end portion 132 of shat 130 is disposed within housing 110. Shaft 130 extends distally from housing 110 through outer sheath connector 120 to distal end portion 134 of shaft 130. Cutting member 140, described in greater detail below, is fixed relative to and extends distally from distal end portion 134 of shaft 130. Drive mechanism 150 is operably supported within body portion 112 of housing 110 and operably coupled to proximal end portion 132 of shaft 130. As also detailed below, drive mechanism 150 is configured to drive rotation of shaft 130 relative to housing 110, thus rotating cutting member 140 relative to housing 110 to resect tissue.

Continuing with reference to FIGS. 1 and 2, outer assembly 200 includes a proximal hub 210, an outer sheath 220, a fluid inflow tube 230, and a valve 240. Proximal hub 210 is configured for positioning about collar 122 of outer sheath connector 120 of tissue resecting instrument 100 and includes suitable engagement features, e.g., female bayonet connectors (not shown), to enable releasable engagement of proximal hub 210 about outer sheath connector 120 and, thus, releasable engagement of outer assembly 200 about tissue resecting instrument 100. Outer sheath 220 is fixed relative to and extends distally from proximal hub 210. Upon engagement of outer assembly 200 about tissue resecting instrument 100, outer sheath 220 of outer assembly 200 is disposed about shaft 130 of tissue resecting instrument 100 so as to define an annular channel 222 (FIG. 3A) between shaft 130 and outer sheath 220. Fluid inflow tube 230 of outer assembly 200 is operably and, in some embodiments, releasably, coupled to proximal hub 210 with valve 240 disposed therebetween to enable fluid to be pumped from fluid supply reservoir 310 into proximal hub 210 and through annular channel 222 (FIG. 3A) by way of fluid pump 300.

Figure 3A:
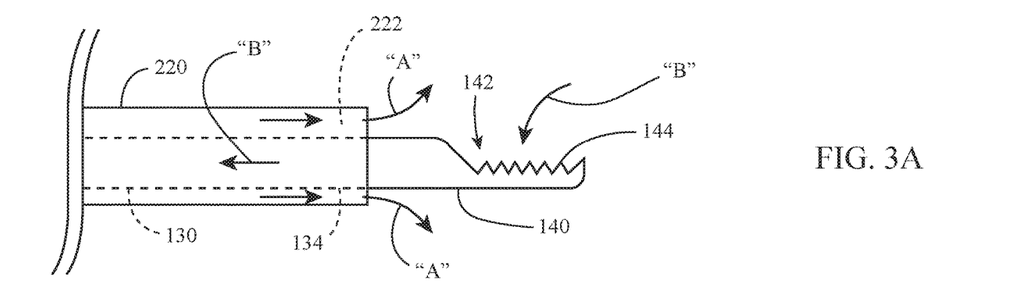
FIG. 3A is a side view of the distal end portion of the tissue resecting system of FIG. 1.

With additional reference to FIG. 3A, cutting member 140 of tissue resecting instrument 100 defines an opening 142 providing access to the interior of shaft 130 and a serrated edge 144 surround opening 142, although other suitable cutting edge configurations are also contemplated. In use, inflow fluid is pumped into the surgical site through annular channel 222, as indicated by arrows "A" and outflow fluid is suctioned, along with tissue and other debris, into opening 142 of cutting member 140 and through shaft 130, as indicated by arrows "B." The suctioning of tissue into opening 142, in combination with the rotation imparted to cutting member 140 by drive mechanism 150 (FIG. 2), enables the resection of tissue using serrated edge 144 and the suctioning of the resected tissue proximally through shaft 130. Other suitable configurations of the distal end portion of tissue resecting instrument 100 to facilitate tissue resection and suctioning of the resected tissue proximally through tissue resecting instrument 100 are also contemplated such as, for example, those detailed below with reference to FIGS. 3B-3D.

Figure 3B:
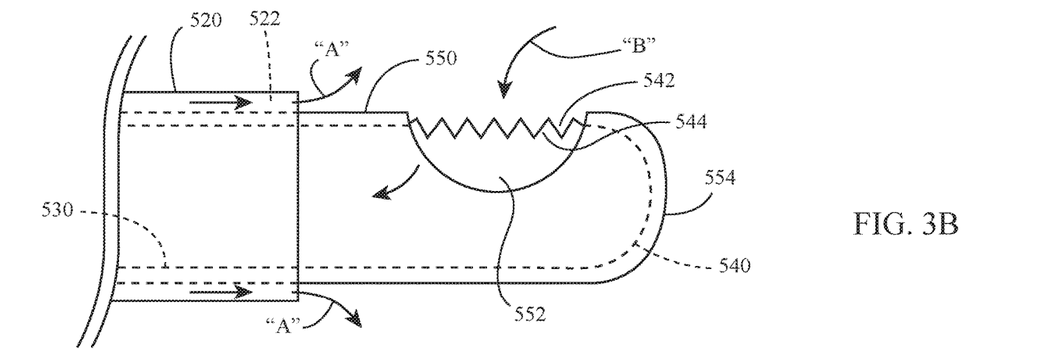
FIGS. 3B-3D are side views of other distal end portion configurations for use with the tissue resecting system of FIG. 1.

Referring to FIG. 3B, another configuration of the distal end portion of tissue resecting instrument 100 (FIG. 1) is provided wherein shaft 530 includes a cutting member 540 extending distally therefrom, and wherein a fixed outer tube 550 is disposed about shaft 530 and cutting member 540. Alternatively, outer tube 550 may be rotatable and shaft 530 fixed, or outer tube 550 and shaft 530 may be rotatable in opposite directions relative to one another. Fixed outer tube 550 is fixedly secured to housing 110 (FIG. 1) and defines an opening 552 extending through a side wall thereof towards closed distal end 554 thereof. Opening 552 provides access to cutting member 540 within the interior of outer tube 550.

Cutting member 540 defines an opening 542 providing access to the interior of shaft 530 and a serrated edge 544 surrounding opening 542, although other suitable cutting edge configurations are also contemplated. In use, inflow fluid is pumped into the surgical site through annular channel 522 defined between outer sheath 520 and fixed outer tube 550, as indicated by arrows "A," and outflow fluid is suctioned, along with tissue and other debris, through opening 552 of outer tube 550 and into opening 542 of cutting member 540, as indicated by arrows "B." The suctioning of tissue into opening 542 of cutting member 540, in combination with the rotation of cutting member 540 relative to outer tube 550, enables the resection of tissue using serrated edge 544 and the suctioning of the resected tissue proximally through shaft 530, along with the outflow fluid and other debris.

Figure 3C:
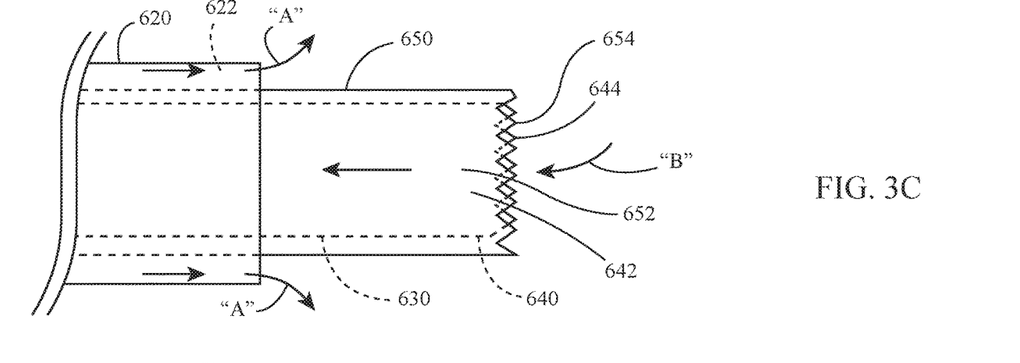

FIG. 3C illustrates another configuration of the distal end portion of tissue resecting instrument 100 (FIG. 1), wherein shaft 630 includes a cutting member 640 extending distally therefrom, and wherein a fixed outer tube 650 is disposed about shaft 630 and cutting member 640. Alternatively, outer tube 640 may be rotatable and shaft 630 fixed, or outer tube 650 and shaft 630 may be rotatable in opposite directions relative to one another. Fixed outer tube 650 is fixedly secured to housing 110 (FIG. 1) and defines an open distal end 652 and a serrated annular distal edge 654 surrounding open distal end 652.

Cutting member 640 defines an open distal end 642 and a serrated annular distal edge 644 surrounding open distal end 642. Serrated annular distal edge 644 of cutting member 640 is positioned in close proximity to serrated annular distal edge 654 of outer tube 650 and, in some embodiments, is positioned such that the serrations on serrated annular distal edge 644 and the serrations on serrated annular distal edge 654 at least partially overlap one another. In use, inflow fluid is pumped into the surgical site through annular channel 622 defined between outer sheath 620 and fixed outer tube 650, as indicated by arrows "A," and outflow fluid is suctioned, along with tissue and other debris, through openings 652, 642 of outer tube 650 and cutting member 640, respectively, as indicated by arrows "B." The suctioning of tissue into opening 642 of cutting member 640, in combination with the rotation of cutting member 640 relative to outer tube 650, enables the resection of tissue using serrated edges 644, 654 and the suctioning of the resected tissue proximally through shaft 630, along with the outflow fluid and other debris.

Figure 3D:
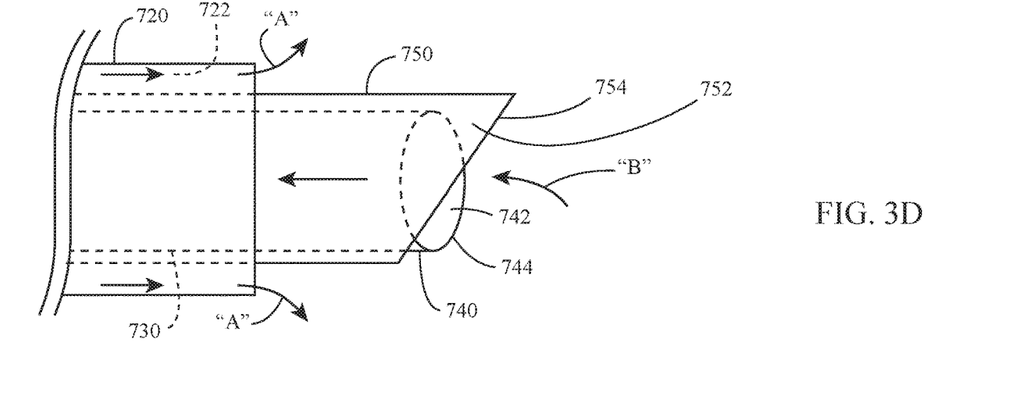

With reference to FIG. 3D, another configuration of the distal end portion of tissue resecting instrument 100 (FIG. 1) is provided, wherein shaft 730 includes a cutting member 740 extending distally therefrom, and wherein a fixed outer tube 750 is disposed about shaft 730 and cutting member 740. Alternatively, outer tube 750 may be rotatable and shaft 730 fixed, or outer tube 750 and shaft 730 may be rotatable in opposite directions relative to one another. Fixed outer tube 750 is fixedly secured to housing 110 (FIG. 1) and defines an open distal end 752 and a beveled distal edge 754 surrounding open distal end 752. Beveled distal edge 754 may be sharpened so as to serve as a cutting edge, or may be blunt.

Cutting member 740 defines an open distal end 742 and an annular distal edge 744 surrounding open distal end 742. Annular distal edge 744 may be sharpened so as to serve as a cutting edge, or may be blunt. Cutting member 740 extends partially from outer tube 740 such that annular distal edge 744 is exposed towards one side of beveled distal edge 754 of outer tube 750 but is recessed within beveled distal edge 754 of outer tube 750 towards the other side thereof. In use, inflow fluid is pumped into the surgical site through annular channel 722 defined between outer sheath 720 and outer tube 750, as indicated by arrows "A," and outflow fluid is suctioned, along with tissue and other debris, through openings 752, 742 of outer tube 750 and cutting member 740, respectively, as indicated by arrows "B." The suctioning of tissue into opening 742 of cutting member 740, in combination with the rotation of cutting member 740 relative to outer tube 750, enables the resection of tissue using annular distal edge 744 and/or beveled distal edge 754 and the suctioning of the resected tissue proximally through shaft 730, along with the outflow fluid and other debris.

Figure 4:
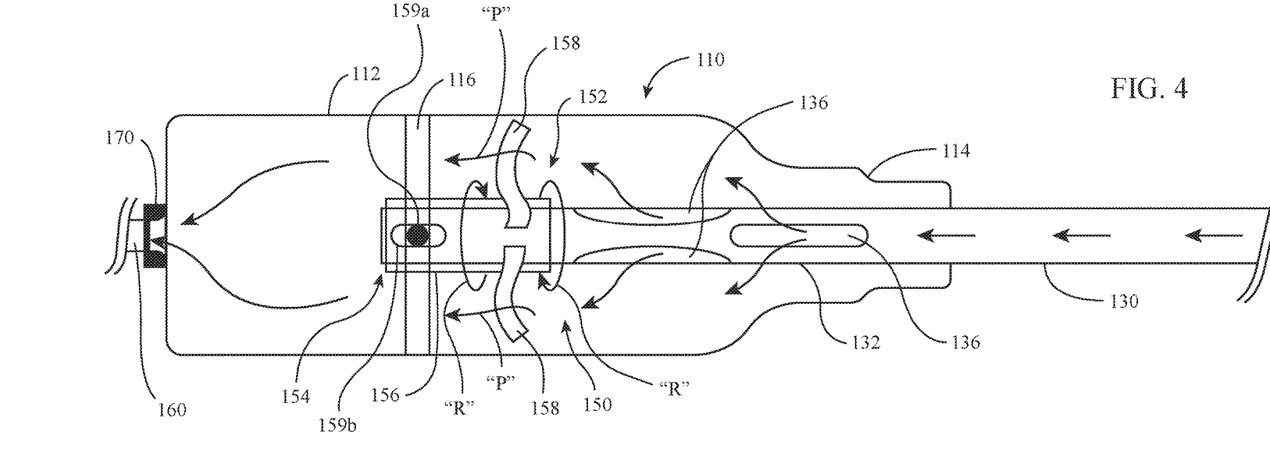
FIG. 4 is a longitudinal, cross-sectional view of the proximal end portion of the tissue resecting instrument of the tissue resecting system of FIG. 1.
Figure 5A:
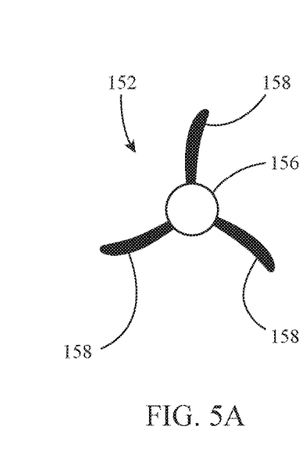
FIG. 5A is a front view of the turbine of the drive mechanism of the tissue resecting instrument of the tissue resecting system of FIG. 1.

Turning to FIGS. 3A, 4, and 5A, as noted above, tissue resecting instrument 100 includes drive mechanism 150 which is operably supported within housing 110 and operably coupled to proximal end portion 132 of shaft 130. Drive mechanism 150, more specifically, includes a turbine 152 and a thrust coupling 154. Turbine 152, in some embodiments, includes a tubular body 156 and a plurality of propeller blade-like fins 158. Tubular body 156 is disposed about proximal end portion 132 of shaft 130 within housing 110, while the plurality of fins 158 are engaged to, annularly spaced about, and extend radially outwardly from tubular body 156 within housing 110. Fins 158 are configured such that the flow of the outflow fluid proximally through housing 110, as indicated by arrows "P," urges fins 158 to rotate, as indicated by arrows "R," thereby similarly rotating tubular body 156. Other suitable turbine configurations are also contemplated such as, for example, those detailed below with reference to FIGS. 5B and 5C.

Thrust coupling 154 couples tubular body 156 with proximal end portion 132 of shaft 130 such that rotation of tubular body 156 effects rotation of shaft 130 and, thus, cutting member 140 (FIG. 3A), about its longitudinal axis, as indicated by arrows "R." Thrust coupling 154, more specifically, includes a transverse pin 159a extending transversely through proximal end portion 132 of shaft 130 and outwardly from either side thereof. The ends of transverse pin 159a extend through opposed longitudinal slots 159b defined within tubular body 156 of turbine 152 and are received within an annular track 116 defined on an interior surface of housing 110. Receipt of transverse pin 159a within annular track 116 inhibits translation of transverse pin 159a and, thus, shaft 130 relative to housing 110 while permitting rotation of transverse pin 159a and shaft 130 relative to housing 110. With transverse pin 159a extending through opposed longitudinal slots 159b of tubular body 156 of turbine 152, turbine 152 is confined to a small amount of translation relative to shaft 130 and housing 110, e.g., as defined by the length of longitudinal slots 159b, to provide some play therebetween and absorb axial load imparted thereto. Further, with transverse pin 159a extending through proximal end portion 132 of shaft 130 and opposed longitudinal slots 159b of tubular body 156 of turbine 152, transverse pin 159a serves to engage shaft 130 and turbine 152 with one another such that rotation of turbine 152 effects corresponding rotation of shaft 130. One or more biasing members (not shown) may further be provided to bias transverse pin 159a towards a particular position within longitudinal slots 159b. Other suitable thrust couplings, e.g., thrust bearings, configured to enable rotation while also supporting axial load are also contemplated. Alternatively, rather than providing a thrust coupling, tubular body 156 may be rigidly coupled to proximal end portion 132 of shaft 130.

Figure 5B:
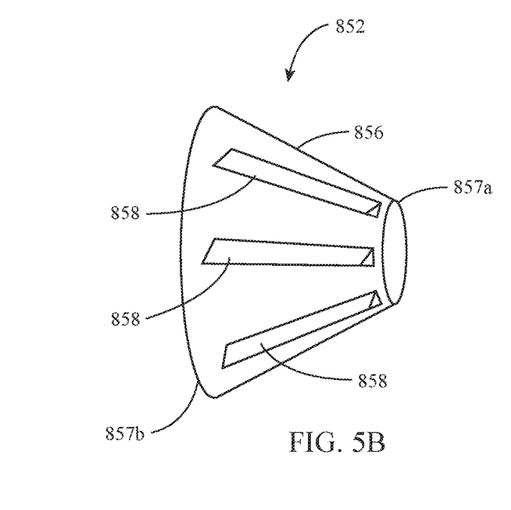
FIG. 5B is a side view of another turbine configured for use with the tissue resecting instrument of the tissue resecting system of FIG. 1.

Referring to FIG. 5B, another turbine configured for use with tissue resecting instrument 100 (FIG. 1) is identified by reference numeral 852. Turbine 852 includes a conical body 856 and a plurality of elongated fins 858. Turbine 852 may be coupled to proximal end portion 132 of shaft 130 within housing 110 (see FIG. 4) via a thrust coupling or via a rigid connection. In use with tissue resecting instrument 100 (FIG. 1), conical body 856 of turbine 852 is oriented such that nose 857a of conical body 856 is more-distally disposed, while base 857b of conical body 856 is more-proximally disposed. Fins 858 are engaged to, spaced about, and extend longitudinal along and outwardly from conical body 856. Fins 858 are configured such that the flow of the outflow fluid proximally through housing 110, as indicated by arrows "P" (see FIG. 4), urges fins 858 to rotate, as indicated by arrows "R" (see FIG. 4), thereby similarly rotating tubular body 856.

Figure 5C:
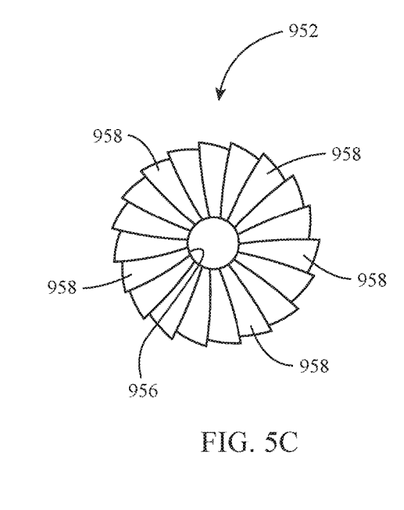
FIG. 5C is a front view of another turbine configured for use with the tissue resecting instrument of the tissue resecting system of FIG. 1.

FIG. 5C illustrates another turbine configured for use with tissue resecting instrument 100 (FIG. 1) identified by reference numeral 952. Turbine 952 includes a tubular body 956 and a plurality of overlapping jet engine blade-like fins 958. Turbine 952 may be coupled to proximal end portion 132 of shaft 130 within housing 110 (see FIG. 4) via a thrust coupling or via a rigid connection. Fins 958 are engaged to and annularly disposed about conical body 956 in overlapping relation relative to one another. Fins 958 are configured such that the flow of the outflow fluid proximally through housing 110, as indicated by arrows "P" (see FIG. 4), urges fins 958 to rotate, as indicated by arrows "R" (see FIG. 4), thereby similarly rotating tubular body 956.

Figure 6:
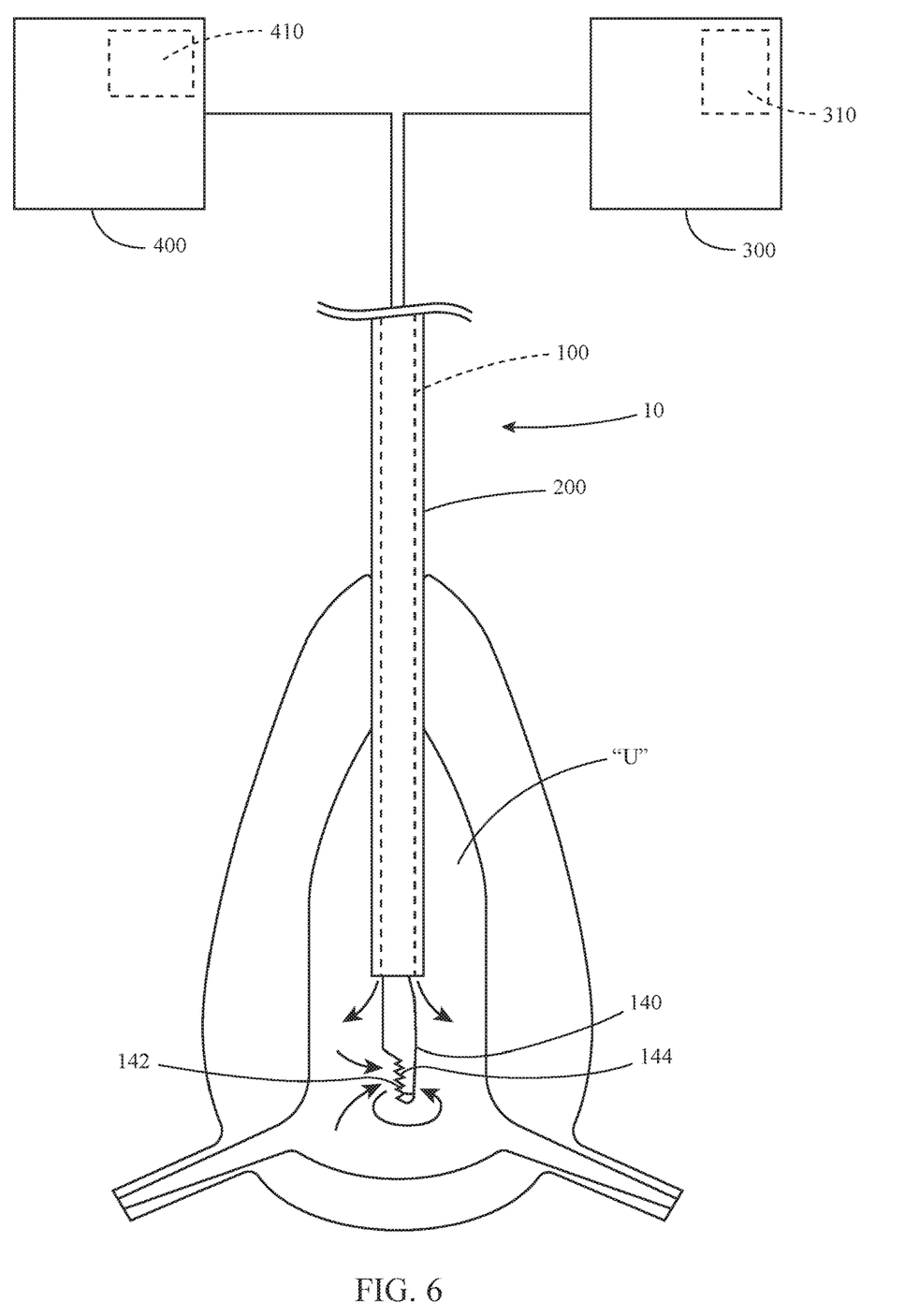
FIG. 6 is a side view of the tissue resecting system of FIG. 1 shown positioned within a uterus for resecting tissue therefrom.

Referring to FIGS. 1, 2, and 6, in use, tissue resecting instrument 100, with outer assembly 200 disposed thereon, is positioned within an internal body cavity or organ, e.g., a uterus "U." Once positioned in this manner, fluid pump 300 is activated to pump inflow fluid from fluid supply reservoir 310 into the uterus "U" to distend the uterus "U." Suction source 400 is also activated, to suction fluid from the uterus "U" through tissue resecting instrument 100 and into fluid collecting reservoir 410. The pumping of inflow fluid and suctioning of outflow fluid may continue simultaneously throughout the procedure in order to achieve continuous flow during the procedure.

With additional reference to FIG. 4, as noted above, the outflow fluid flows proximally through tissue resecting instrument 100 under suction from suction source 400. More specifically, suction source 400 suctions the outflow fluid into opening 142 of cutting member 140 and through shaft 130. The outflow fluid is suctioned proximally through shaft 130 and enters housing 110 via a plurality of openings 136 defined within shaft 130 towards proximal end portion 132 thereof. The outflow fluid is further suctioned proximally through housing 110 and into fluid outflow tube 160, through which the outflow fluid travels to fluid collecting reservoir 410.

The suction force provided by suction source 400 to suction the outflow fluid into cutting member 140 and proximally through housing 110 establishes sufficient fluid flow through housing 110 and proximally across fins 158 of turbine 152 to urge turbine 152 to rotate, thereby rotating shaft 130 and cutting member 140. With cutting member 140 rotating and suction source 400 suctioning tissue into cutting member 140, tissue is resected and removed from the uterus "U" through tissue resecting instrument 100. Thus, rather than the need for a separate drive source, e.g., a motor, for driving rotation of cutting member 140, cutting member 140 is driven by the proximal flow of outflow fluid under suction.

Although resected tissue and other debris are also suctioned into cutting member 140 and through shaft 130, housing 110, fluid outflow tube 160, and into fluid collecting reservoir 410 (FIG. 1), the cutting provided by cutting member 140 creates sufficiently small pieces of resected tissue and other debris so as not to interfere with turbine 152 or alter the rotation imparted thereto by the proximally-flowing outflow fluid. Alternatively, filters (not shown) may be extend across openings 136 such that only fluid exits openings 136 of shaft 130 and flows proximally over fins 158 of turbine 152, while the resected tissue and other debris are suctioned proximally through the open proximal end of shaft 130, housing 110, and into fluid outflow tube 160, thus bypassing turbine 152.

Referring again to FIG. 6, once tissue is resected and removed, fluid pump 300 and suction source 400 may be deactivated and tissue resecting instrument 100, together with outer assembly 200, removed from the uterus "U."

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A method of resecting tissue, comprising:
    positioning a tissue resecting instrument such that a cutting member of the tissue resecting instrument is disposed within an internal surgical site adjacent tissue to be resected, the tissue resecting instrument including a turbine operably associated with the cutting member, the turbine disposed within a fluid outflow path of the tissue resecting instrument;
    pumping fluid distally into the internal surgical site; and
    suctioning fluid proximally out of the internal surgical site through the fluid outflow path of the tissue resecting instrument,
    wherein proximal fluid flow across the turbine urges the turbine to rotate, thereby rotating the cutting member to resect tissue adjacent thereto;
    wherein pumping fluid distally includes pumping fluid distally through an annular channel defined between a shaft of the tissue resecting instrument and an outer sheath disposed about the shaft;
    wherein the fluid outflow path extends through the shaft of the tissue resecting instrument, and wherein the distally pumped fluid flows proximally through the fluid outflow path to the turbine;
    wherein the annular channel is fluidly separated from the fluid outflow path along the outer sheath of the fluid resecting instrument such that the distally pumped fluid does not enter the fluid outflow path until after reaching the internal surgical site.

2. The method according to claim 1, wherein suctioning fluid proximally suctions tissue into the cutting member such that the rotation of the cutting member resects tissue disposed therein, the resected tissue suctioned though the fluid outflow path of the tissue resecting instrument along with fluid.

3. The method according to claim 1, wherein:
    pumping fluid distally includes pumping fluid from a fluid supply reservoir distally into the internal surgical site; and
    suctioning fluid proximally includes suctioning fluid proximally out of the internal surgical site through the fluid outflow path of the tissue resecting instrument to a fluid collection reservoir.

4. The method according to claim 1, wherein the turbine includes a plurality of laterally-extending fins, and wherein the proximally suctioned fluid passes over the plurality of laterally-extending fins to urge the turbine to rotate.

5. The method according to claim 1, wherein the turbine includes a plurality of elongated fins, and wherein the proximally suctioned fluid passes over the plurality of elongated fins to urge the turbine to rotate.

6. The method according to claim 1, wherein the turbine is configured to rotate in a first direction, and wherein the cutting member of the tissue resecting instrument is configured to rotate in a second direction opposite the first direction.

7. The method according to claim 6, wherein rotation of the turbine in the first direction causes a corresponding rotation of the cutting member of the tissue resecting instrument in the second direction.

8. The method according to claim 1, wherein the turbine includes a plurality of blade-shaped fins, and wherein the proximally suctioned fluid passes over the plurality of blade-shaped fins to urge the turbine to rotate.

9. A method of resecting tissue, comprising:
    positioning a tissue resecting instrument such that a cutting member of the tissue resecting instrument is disposed within an internal surgical site, the tissue resecting instrument including a housing and a shaft extending distally from the housing, the shaft supporting the cutting member at a distal end thereof, the shaft defining a lumen extending from the housing to the cutting member, and the shaft defining a hole connecting the lumen with an inner space of the housing, the tissue resecting instrument including a turbine operably associated with the cutting member, the turbine disposed in the inner space of the housing, wherein the tissue resecting instrument defines a fluid outflow path from the internal surgical site, through the lumen, and to the turbine;
    pumping fluid distally into the internal surgical site; and
    suctioning fluid proximally out of the internal surgical site through the fluid outflow path of the tissue resecting instrument,
    wherein proximal fluid flow across the turbine urges the turbine to rotate, thereby rotating the cutting member of the tissue resecting instrument.

10. The method according to claim 9, wherein pumping fluid distally includes pumping fluid distally through an annular channel defined between the shaft of the tissue resecting instrument and an outer sheath disposed about the shaft.

11. The method according to claim 10, wherein the annular channel is fluidly separated from the fluid outflow path along the outer sheath of the fluid resecting instrument such that the distally pumped fluid does not enter the fluid outflow path until after reaching the internal surgical site.

12. The method according to claim 9, wherein:
pumping fluid distally includes pumping fluid from a fluid supply reservoir distally into the internal surgical site; and
suctioning fluid proximally includes suctioning fluid proximally out of the internal surgical site through the fluid outflow path of the tissue resecting instrument to a fluid collection reservoir.

13. The method according to claim 9, wherein the turbine includes a plurality of laterally-extending fins, and wherein the proximally suctioned fluid passes over the plurality of laterally-extending fins to urge the turbine to rotate.

14. The method according to claim 9, wherein the turbine includes a plurality of elongated fins, and wherein the proximally suctioned fluid passes over the plurality of elongated fins to urge the turbine to rotate.

15. The method according to claim 9, wherein the turbine is configured to rotate in a first direction, and wherein the cutting member of the tissue resecting instrument is configured to rotate in a second direction opposite the first direction.

16. The method according to claim 15, wherein rotation of the turbine in the first direction causes a corresponding rotation of the cutting member of the tissue resecting instrument in the second direction.

17. The method according to claim 9, wherein the turbine includes a plurality of blade-shaped fins, and wherein the proximally suctioned fluid passes over the plurality of blade-shaped fins to urge the turbine to rotate.

* * * * *